(12) United States Patent
Allerdings

(10) Patent No.: US 11,315,670 B2
(45) Date of Patent: Apr. 26, 2022

(54) METHOD AND MONITORING DEVICE FOR MONITORING OPERATION OF A DRUG DELIVERY DEVICE

(71) Applicant: Sanofi-Aventis Deutschland GMBH, Frankfurt am Main (DE)

(72) Inventor: Alexander Allerdings, Frankfurt am Main (DE)

(73) Assignee: Sanofi-Aventis Deutschland GMBH, Frankfurt am Main (DE)

(\*) Notice: Subject to any disclaimer, the term of this patent is extended or adjusted under 35 U.S.C. 154(b) by 200 days.

(21) Appl. No.: 16/520,732

(22) Filed: Jul. 24, 2019

(65) Prior Publication Data
US 2019/0365989 A1 Dec. 5, 2019

Related U.S. Application Data

(62) Division of application No. 14/240,796, filed as application No. PCT/EP2012/067548 on Sep. 7, 2012, now Pat. No. 10,383,998.

(30) Foreign Application Priority Data

Sep. 8, 2011 (EP) ..................... 1180590

(51) Int. Cl.
*G16H 20/17* (2018.01)
*A61M 5/315* (2006.01)
(Continued)

(52) U.S. Cl.
CPC ............ *G16H 20/17* (2018.01); *A61M 5/168* (2013.01); *A61M 5/31525* (2013.01);
(Continued)

(58) Field of Classification Search
CPC .............. A61M 5/31525; A61M 5/168; A61M 5/31533; A61M 2205/3317;
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

EP 0937471 8/1999
EP 0937476 8/1999
(Continued)

OTHER PUBLICATIONS

Halperin, Daniel, Hu, Wenjun, Sheth, Anmol, Weitherall, David; 802.11 with Multiple Antennas for Dummies; Jan. 2010; ACM SIGCOMM Computer Communication Review; vol. 40, No. 1; pp. 19-25; https://www.cs.princeton.edu/courses/archive/spring19/cos463/papers/dummies.pdf (Year: 2010).*
(Continued)

*Primary Examiner* — Bradley J Osinski
(74) *Attorney, Agent, or Firm* — Fish & Richardson P.C.

(57) ABSTRACT

The present invention relates to a method and to a monitoring device for monitoring operation of a drug delivery device, the monitoring device comprising of at least a first and a second sensor arranged at a distance from each other with regard to a first direction and being adapted to generate a first and a second electrical signal in response to an operation of the device, a processing unit configured to determine a time delay between the first and the second electrical signals and being adapted to determine at least one state parameter of the drug delivery device on the basis of said time delay.

19 Claims, 4 Drawing Sheets

(51) Int. Cl.
*G16H 40/67* (2018.01)
*A61M 5/168* (2006.01)
*A61M 5/24* (2006.01)
*G01N 29/14* (2006.01)

(52) U.S. Cl.
CPC ........ *A61M 5/31533* (2013.01); *G16H 40/67* (2018.01); *A61M 5/24* (2013.01); *A61M 2205/3317* (2013.01); *A61M 2205/3375* (2013.01); *A61M 2205/581* (2013.01); *A61M 2205/582* (2013.01); *G01N 29/14* (2013.01)

(58) Field of Classification Search
CPC .... A61M 2205/3375; A61M 2205/581; A61M 2205/582; G01N 29/14
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,473,942 A | 12/1995 | Vick et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Detersen et al. | |
| 5,651,775 A | 7/1997 | Walker | |
| 5,674,204 A | 10/1997 | Chanoch | |
| 5,688,251 A | 11/1997 | Chanoch | |
| 5,921,966 A | 7/1999 | Bendek | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,482,185 B1 | 11/2002 | Hartmann | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2008/0243088 A1* | 10/2008 | Evans | A61M 5/31565 604/246 |
| 2008/0306443 A1 | 12/2008 | Neer et al. | |
| 2009/0069742 A1 | 3/2009 | Larsen | |
| 2009/0275916 A1 | 11/2009 | Harms et al. | |
| 2010/0066496 A1* | 3/2010 | Cho | H04Q 9/00 340/10.1 |
| 2010/0114040 A1 | 5/2010 | Schriver | |
| 2011/0295215 A1 | 12/2011 | Nielsen | |
| 2013/0228171 A1 | 9/2013 | Mansfield | |
| 2013/0320094 A1 | 12/2013 | Slusar | |

FOREIGN PATENT DOCUMENTS

| | | |
|---|---|---|
| EP | 1603611 | 5/2008 |
| JP | 2000-046610 | 2/2000 |
| WO | 1999/38554 | 8/1999 |
| WO | 2001/10484 | 2/2001 |
| WO | 2007/107564 | 9/2007 |
| WO | 2011/117212 | 9/2011 |

OTHER PUBLICATIONS

International Search Report for Int. App. No. PCT/EP2012/067548, completed Sep. 21, 2012, 10 pages.
International Preliminary Report on Patentability in International Application No. PCT/EP2012/067548, dated Mar. 12, 2014.

* cited by examiner

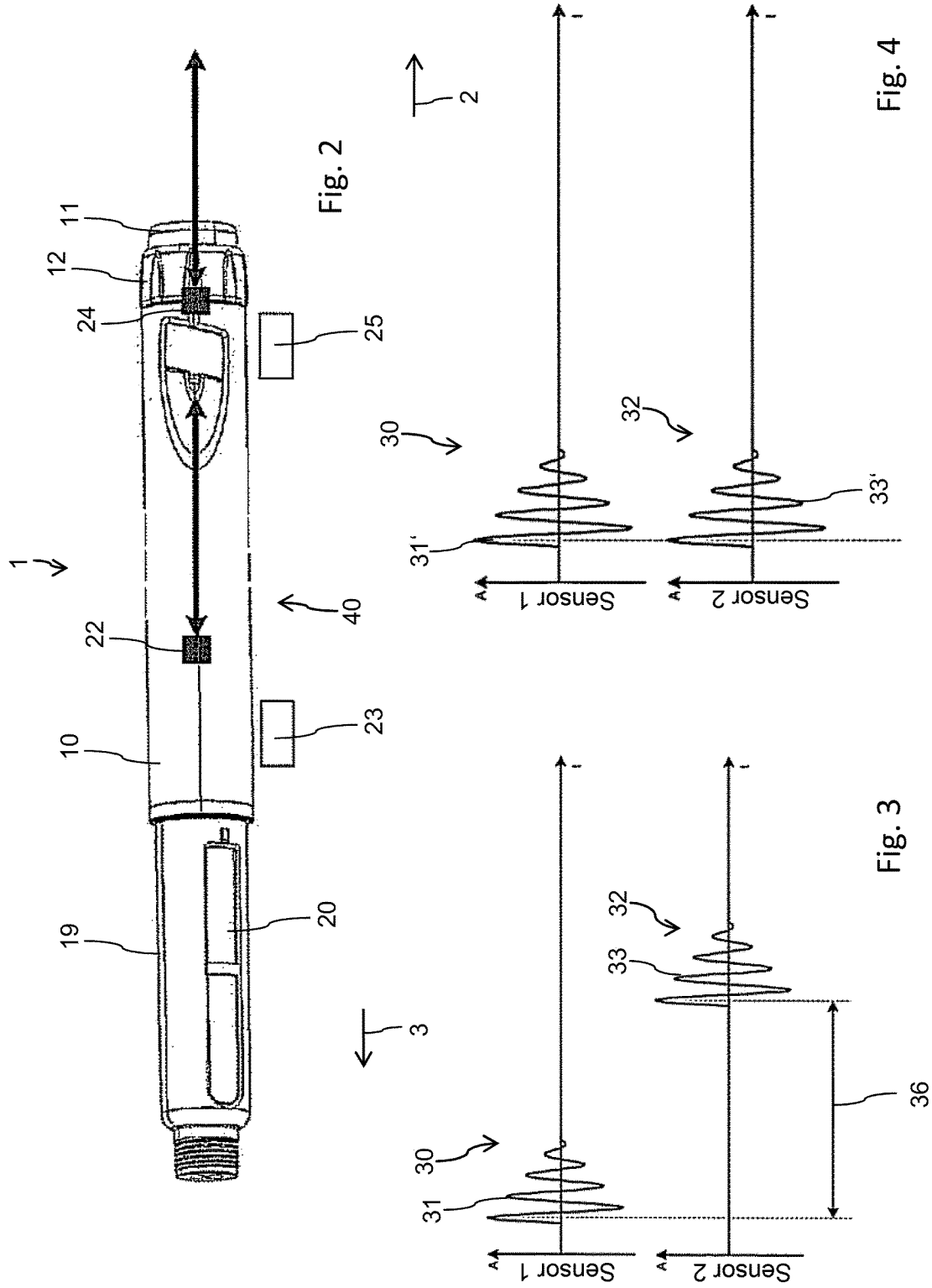

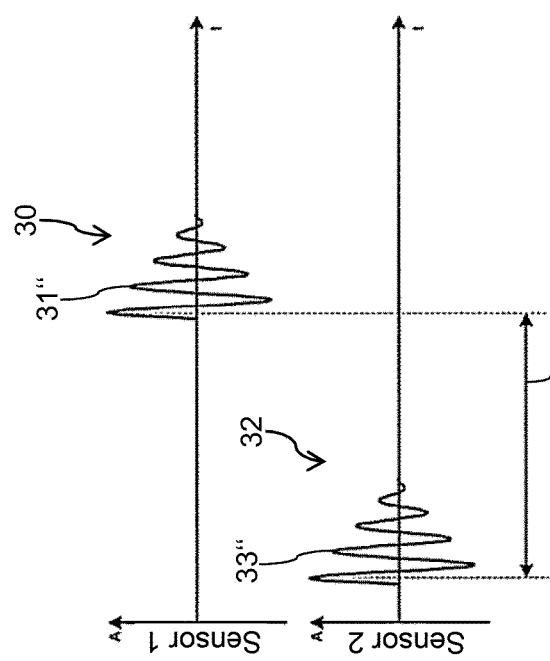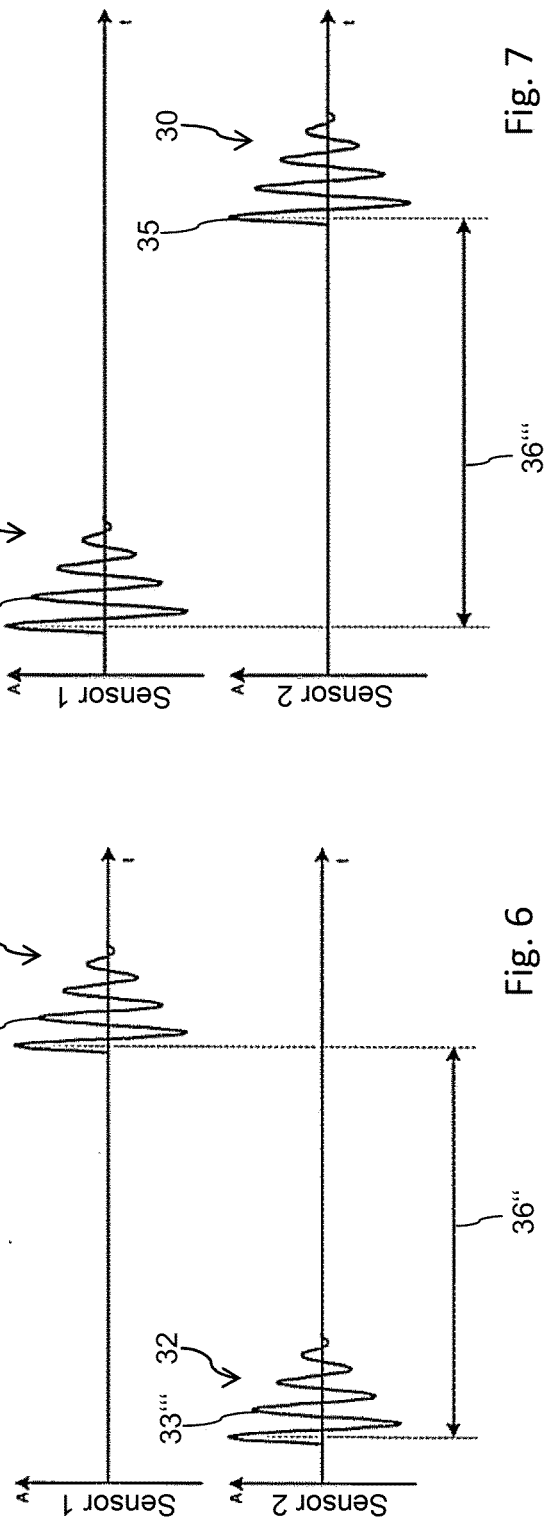

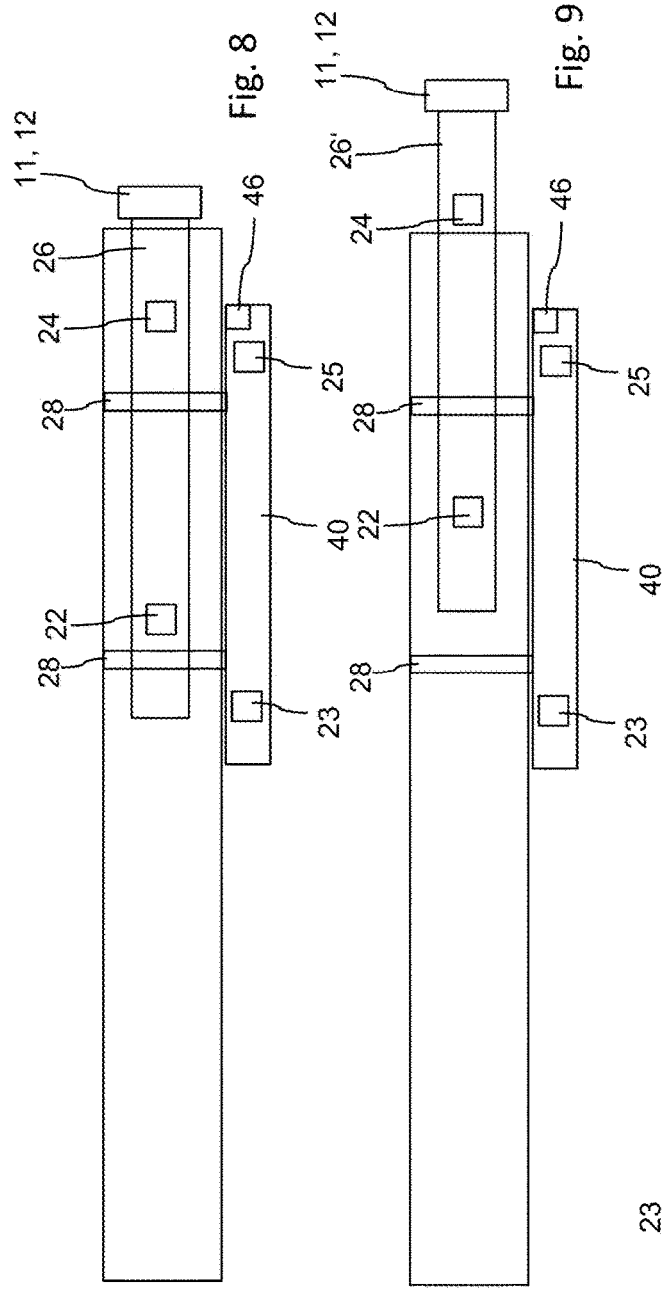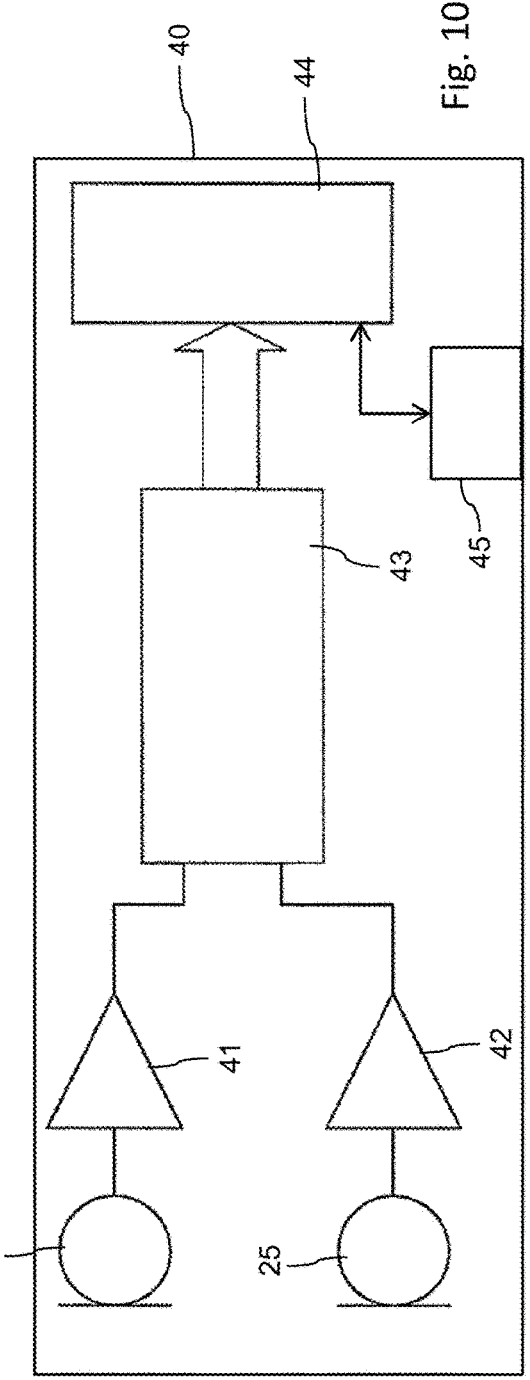

METHOD AND MONITORING DEVICE FOR MONITORING OPERATION OF A DRUG DELIVERY DEVICE

CROSS REFERENCE TO RELATED APPLICATIONS

The present application is a divisional of U.S. patent application Ser. No. 14/240,796, filed Feb. 25, 2014, which is a U.S. National Phase Application pursuant to 35 U.S.C. § 371 of International Application No. PCT/EP2012/067548 filed Sep. 7, 2012, which claims priority to European Patent Application No. 11180590.9 filed Sep. 8, 2011. The entire disclosure contents of these applications are herewith incorporated by reference into the present application.

TECHNICAL FIELD

The present invention relates to the field of drug delivery devices and in particular to injection devices designed and intended for regular and long-term self-medication. In particular, the invention refers to a monitoring device adapted to monitor and to log or to record usage and handling of the drug delivery device.

BACKGROUND

Chronic diseases require administering of medicaments or drugs according to a pre-defined time schedule in order to keep the concentration level of a pharmaceutically active substance on a pre-defined level. Many medicaments require administration by way of injection by making use of syringes or syringe-like drug delivery devices. Such devices should be universally applicable and should be operable even by persons without formal medical training.

Moreover, such devices, like pen-type injectors should provide accurate, precise and reliable setting of a dose and subsequent dispensing of the respective medicament. Typically, the medicament to be dispensed and injected is provided in a disposable or replaceable cartridge, such as a vial, an ampoule or a carpule comprising a slidably disposed piston to become operably engaged with a piston rod of a drive mechanism of the drug delivery device. The drive mechanism is adapted to apply thrust to the cartridge's piston in distal direction in order to built-up a respective fluid pressure, which in turn leads to a dispensing of the liquid medicament via a dispensing or distal end of the cartridge being typically in fluid connection with a piercing element like an injection needle.

It is generally of importance, that the patient strictly follows a given prescription schedule. However, patients that already got used to the medicament for a long time or patients that suffer side effects of a chronic disease and which may be physically impaired, compliance of the prescription schedule is sometimes sub-optimal. Since a large variety of existing drug delivery devices is implemented all-mechanically, it is further rather difficult for an attending physician to control, whether the patient strictly follows the prescription schedule.

From document WO 2007/107564 A1 an electronic module is known, which is to be positioned on an outer surface of a pen-like medication delivery device. The electronic module is capable of measuring signals, such as audible, optical, vibration or electromagnetic signals, generated during operation of a pen-like medication delivery device. By way of detecting acoustic signals generated in response to setting of a dose of a medicament or generated in response to expelling a dose of the medicament, respective information can be gathered and stored in the electronic module, which allow to monitor frequent usage and operation of the drug delivery device.

Hence, the known electronic device may detect different "click-sounds" being indicative of a dose setting or of a dose dispensing procedure, respectively. However, such an electronic module is so far unable to precisely determine the size of a dose and the corresponding amount of the respective medicament dispensed from the device during an injection operation.

It is therefore an object of the present invention to provide an improved monitoring device allowing for contactless and quantitative determination of a dose set and/or to be dispensed by a drug delivery device. Moreover, the monitoring device should provide an elegant, reliable and precise approach to unequivocally detect and to identify one or more parameters, for example state parameters, or configurations of the drug delivery device, being preferably implemented in an all-mechanical way.

SUMMARY

In a first aspect, the invention provides a monitoring device for monitoring operation of a drug delivery device. The monitoring device is particularly adapted for contactless and/or wireless monitoring of subsequent device operations. The monitoring device typically provided as a separate unit to be coupled and/or interconnected with the housing of the drug delivery device comprises at least a first and a second sensor arranged at a distance from each other with regard to a first direction, e.g. a longitudinal direction. The two sensors are each adapted to generate a first and a second electrical signal in response to an operation of the device.

Typically, the two sensors are adapted to detect and/or to record one and the same detectable operation of the device. The sensors are further coupled with a processing unit of the monitoring device which is adapted to determine a time delay between the first and the second electrical signals generated by first and second sensors, respectively. On the basis of this time delay, the processing unit is further adapted to determine at least one parameter, for example a state parameter, of the drug delivery device.

The monitoring device is suitable and designed for drug delivery devices, wherein setting and/or dispensing of a dose is accompanied by device-specific or by device-characteristic features that are detectable outside the device by way of the monitoring device. Said features may express in a visual, audible and/or haptic way. They are typically generated by a particular component of the drive mechanism of the drug delivery device, which is preferably subject to a displacement or movement along the first direction during dose setting and/or dose dispensing.

By making use of two different sensors separated from each other along the first direction, a varying or moving place of origin of the detectable signal during operation of the drug delivery device and/or of its drive mechanism along the first direction can be detected. The displacement of the signal generating component of the drive mechanism reflects in a time delay between the signals detected or recorded by first and second sensors, respectively. From the detected or measured time delay, a relative position of the signal generation component of the drive mechanism relative to the position of first and second sensors can be derived. The position of the signal generating component of the drive mechanism is typically indicative of the configuration of the drive mechanism from which e.g. the actual size of a dose can be calculated or determined.

According to a preferred embodiment, the first and/or the second sensors comprise an acoustic-, a vibration-, an acceleration- and/or a mechanical tension sensing element. Preferably, the sensors are designed as acoustic or vibrational sensors by way of which a characteristic click-sound of the drive mechanism can be detected. Depending on the relative position of a click-sound generating component of the drive mechanism and the two respective sensors, for instance an audible signal provided by the drive mechanism may be almost simultaneously detected at the location of two detectors, with a time delay typically in the range of microseconds.

Operation of the drug delivery device, either for dose setting or dose dispensing typically leads to a displacement of the click-sound generating component of its drive mechanism, thus leading to a respective modification of the time delay. For instance, zero time delay between first and second electrical signals corresponds to a configuration, wherein the click-sound generating component of the drug delivery device is substantially equally spaced from first and second sensors. A positive time delay corresponds to configurations, wherein the click-sound generating component of the drive mechanism is arranged closer to the first sensor than to the second sensor. A negative time delay corresponds to a configuration, wherein the click-sound generating component is arranged nearer to the second sensor than to the first sensor.

Correspondingly, a positive time delay may be therefore indicative of a rather small dose size, zero time delay may correspond to a medium dose size and a negative time delay may represent a rather large dose size, or vice versa.

Depending on the precision of the detectors and the signal processing of the processing unit, the magnitude of the detected time delay between first and second electrical signals may be precisely correlated with the respective dose size. This way, by making use of two sensors and by evaluating a time delay between them, the size of a set dose in an all-mechanically implemented drug delivery device can be quantitatively and precisely determined in a cost-efficient way. Hence, dose size determination does not require any modifications to a mechanically implemented drug delivery device. It is only required, that the monitoring device is connected with the housing of the drug delivery device in a pre-defined and signal transferring manner.

Even though the invention is preferably described in terms of audible and acoustic signals, the basic concept of the invention can be generally implemented also on the basis of vibrational signals, as well as with acceleration- and mechanical tension-signals. Signal propagation velocity within the housing of the drug delivery device should be in a range allowing to detect a time delay.

Propagation of sound signals, vibrational signals or other mechanical waves propagating in the housing of the drug delivery device should be precisely detectable by the first and second sensors. Moreover, the type of signal to be detected as well as the material, the respective signal wave is propagating through should allow for detection of a time delay. For instance with thermoplastic housing components and with acoustic waves featuring a velocity of propagation in the range of $10^3$ m/s, detectable time delays between first and second electrical signals are typically in the range of microseconds.

According to a further preferred aspect, the monitoring device further comprises at least one threshold circuit to detect the occurrence of of the first and/or of the second electrical signal generated by first and second sensors exceeding a threshold value, respectively. This way, arrival of e.g. a sound wave at the first or second sensor can be precisely and sharply determined. The threshold circuit, which may comprise a Schmitt-trigger or some other kind of comparator-circuit provides a kind of threshold switch. As soon as the electrical signal generated by first and/or second sensor crosses a pre-defined threshold, the respective threshold circuit generates a maximum signal or a minimum signal to be interpreted by a processing unit as logical one or logical zero.

The signals provided by first and second sensors are preferably separately processed by respective first and second threshold circuits. The signals generated by the threshold circuits are then adapted to start and/or to stop a timer module in order to determine the time delay between them.

According to a further preferred embodiment, the processing unit is adapted to determine the size of a dosage set by the drug delivery device when the time delay is smaller than or equal to a pre-defined dosage value (x). This feature typically implies, that a click-sound generating component of the drug delivery device is disposed between first and second sensors with regard to the first direction. The distance between first and second sensors is selected or determined such, that for any possible dose setting configuration of the drive mechanism the click-sound generating component remains between first and second sensors.

The predefined dosage value (x) is typically governed by the velocity of propagation of sound waves in the housing of the drug delivery device and by the distance of first and second sensors. The pre-defined dosage value is typically smaller than the distance between first and second sensors with respect to the first direction divided by the velocity of propagation of the signal generated by the click-sound generating component.

This way, any time delay being smaller than the pre-defined dosage value (x) is a clear indication that the respective signals arise from a dose-setting related displacement of a click-sound generating component of the drug delivery device.

According to a further preferred embodiment, the processing unit is also adapted to identify and/or to detect a dispensing operation of the drug delivery device when the time delay substantially equals a pre-defined injection value (y). Preferably, another click-sound generating component being indicative of an injection or dispensing operation of the drug delivery device is positioned outside the spatial region delimited by first and second sensors, respectively.

By having the dispensing click-sound generating component arranged outside the distance region of first and second sensors, a respective dispensing clicking sound may always lead to substantially identical time delays, irrespective of the actual position or configuration of the drive mechanism. The pre-defined injection value (y) substantially corresponds to or equals the distance between first and second sensors divided by the velocity of propagation.

The processing unit is accordingly adapted to distinguish and to categorize the various time delays. If the time delay ranges between zero and the predefined dosage value (x), a dose setting of the drug delivery device can be logged and monitored. When a time delay substantially equal to the pre-defined injection value (y) is detected, this is an indication, that a dispensing injection procedure takes place. Accordingly, the monitoring device which is further equipped with an electronic storage as well as with a user interface module may increment a dispensing counter.

Moreover, the processing unit may at least temporally store the actual time delay being smaller than or equal to the pre-defined dosage value. In response of subsequently detecting a dose injection procedure, the actual and/or temporarily stored time delay being smaller than or equal to the pre-defined dosage value can be stored or logged in the memory of the monitoring device, e.g. together with a time stamp, thereby allowing to size of the dose actually dispensed.

According to a further preferred embodiment, the monitoring device comprises a third sensor, adapted to individually determine the size of a dosage set by the drug delivery device. In contrast to the first and/or the second sensors, the third sensor may be implemented optically in order to acquire visual information about the size of the set dosage. Signals generated and/or acquired by the third sensor may be separately provided to the processing unit and may be processed either separately or in combination with the signals provided by the first and/or second sensors, which are preferably implemented acoustically.

Usage of a third sensor is of particular benefit in case when e.g. signals of first and second sensors are ambiguous or lie beyond a predefined range. Then, by way of the third sensor, signals obtained from first and/or second sensors can be unequivocally assigned to a particular type and/or magnitude of a state parameter of the device.

Moreover, in a further preferred embodiment, the processing unit is also able to distinguish and/or to determine the leading and/or the trailing signal of the multiplicity of signals generated by the first and/or second sensor. This way, positive and negative time delays can be obtained being further indicative on the size of the set dosage.

According to a further embodiment, the distance with regard to the first or a longitudinal direction between the first and the second sensor is smaller than or equal to the distance between a first and a second sound generating element of the drug delivery device. This way, a configuration can be attained, wherein at least one sound generating element always remains between first and second sensors for any conceivable configuration of the drive mechanism. The sound generating element sandwiched or disposed between first and second sensors is preferably designed to generate audible signals during a dose setting operation.

According to a further or alternative embodiment, the first and/or the second sensors and/or the processing unit is or are adapted to identify different sounds generated by different sound generating elements of the drug delivery device. In particular, the spectral range of for instance a first click-sound generating element is different from the spectral range of the click-sound generated by a second sound generating element. Assuming that first and second sound generating elements are exclusively adapted to generate respective sounds either during dose setting or during dose dispensing, respective dose setting and dose dispensing procedures can be easily detected by spectral analysis of the sound signals to be detected by the first and/or the second sensor.

Additionally and according to another embodiment, the monitoring device also comprises at least one fastening element to releasably fasten the monitoring device in a pre-defined manner to a housing of the drug delivery device. Monitoring device and housing of the drug delivery device may comprise mutually corresponding fastening members, by way of which the monitoring device can be attached to the drug delivery device in a pre-defined and precise way. By providing the monitoring device as a stand-alone electronic device, it can be used with a plurality of different drug delivery devices, which e.g. by the virtue of their all-mechanical implementation may even be designed as disposable pen-type injectors. This way, the monitoring device, releasably attached to the drug delivery device by the at least one fastening element can be repeatedly used with a series of e.g. disposable and cost-efficient drug delivery devices.

In another but independent aspect, the invention also refers to a monitoring system comprising a drug delivery device. The drug delivery device has a housing and a drive mechanism as well as a cartridge being at least partially filled with a medicament to be dispensed. Dispensing or injection of the medicament requires interaction of the drive mechanism, typically with a proximal seal or piston of the cartridge.

The drive mechanism, which may be implemented all-mechanically comprises at least one sound generating element movably disposed along a first direction relative to the housing. This way, during dose setting as well as during dose dispensing or dose injection, the sound generating element is subject to spatial displacement along said first direction relative to the housing. The monitoring system further comprises a monitoring device as described above being fastened to or at least acoustically coupled with the drug delivery device.

Here, first and second sensors of the monitoring device are adapted to detect the sound generated by the sound generating element of the drive mechanism in response to an operation of the same. By detecting and determining time delays between electrical signals to be generated by first and second sensors, respectively, a relative position of the sound generating element with respect to first and second sensors can be derived. Said relative position is a direct indication of the size of the dose set by the drive mechanism and can therefore at least temporally stored or logged in a storage module of the monitoring device.

In a further embodiment of the monitoring system, the drive mechanism of the drug delivery device comprises a first and a second sound generating element, wherein the first sound generating element is adapted to generate a first click-sound during a dose setting operation of the drive mechanism. In contrast to that, the second sound generating element of the drive mechanism is adapted to generate a second click-sound during a dose dispensing operation. Spectral ranges of first and second click-sounds may even coincide or may vastly overlap. Distinction between dose setting and dose dispensing may be exclusively conducted by determination of the above described time delay.

According to a further preferred embodiment, the monitoring device is fastenable to the housing of the drug delivery device in a pre-defined position and/or orientation, such that the at least one sound generating element of the drive mechanism is located between the first and the second sensors of the monitoring device with regard to the first direction. The distance between first and second sensors of the monitoring device is larger than or equal to a maximum distance, the first sound generating element can be moved during a dose dispensing operation. This way it can be ensured, that the first sound generating element always remains between the first and the second sensors in any conceivable configuration of the drive mechanism.

Moreover, the monitoring device is to be fastened to the housing in such a way that even for all conceivable positions and configurations of the drug delivery device the at least one sound generating element remains in the detection range defined by the first and second sensors. This way, the at least one, preferably both sound generating elements always remain in the spatial range of the arrangement formed by at least first and/or second sensors.

The dose setting operation can be therefore characterized in that the time delay is smaller than or equal to a pre-defined dosage value (x).

According to a further preferred embodiment, the at least one sound generating element, preferably the second sound generating element of the drive mechanism is located outside an intermediate space defined by first and second sensors of the monitoring device with regard to the first direction. The respective sound generating element is preferably located at a rather remote or proximal region of the drive mechanism, which in any conceivable configuration of the drive mechanism is beyond or outside said intermediate space.

A sound generated by this second remote sound generating element leads to a time delay which directly corresponds to the distance of first and second sensors and is therefore indicative of a dispensing operation. The time delay to be detected in response of a click-sound generation with the second sound generating element as origin is substantially constant irrespective of the position of the second sound generating element relative to the monitoring device and its first and second sensors as long as said sound generating element is positioned outside said intermediate space.

In a further independent aspect the invention also relates to a method for monitoring operation of a drug delivery device. The drug delivery device, preferably designed as pen-type injector comprises a housing and a drive mechanism, wherein the drive mechanism is to be operably engaged with a piston of a cartridge disposed in the drug delivery device. The drive mechanism further comprises at least one sound generating element moveably disposed along a first direction relative to the housing. The method of monitoring of the drug delivery device comprises the steps of generating a sound during operation of the drive mechanism and detecting said sound by a first sensor and by a second sensor arranged at a distance from each other with regard to the first direction.

In response to the sound detection, respective first and second electrical signals are generated and a time delay between first and second electrical signals is determined. On the basis of said time delay, at least one state or condition parameter of the drug delivery device is determined or derived. Said method is preferably conducted by way of a monitoring device, e.g. to be releasably fastened to the housing of the drug delivery device in such a way, that first and second sensors of the monitoring device are precisely positioned relative to the at least one sound generating element of the drive mechanism of the drug delivery device.

According to a further embodiment, the magnitude of the time delay is compared to pre-defined dosage and/or pre-defined injection values (x, y) for either determining a size of a set dosage and/or for identifying and/or for detecting a dispensing operation of the drug delivery device. Depending on whether a dose size or an injection procedure has been determined, the dose size can be associated with a time stamp and can be stored in an electronic memory module of the monitoring device. This way and by means of appropriate storage reading devices, the actual dosing schedule conducted with an all-mechanically implemented drug delivery device can be precisely monitored and displayed to e.g. an attending physician.

It is further to be noted, that all features and embodiments as described herein are understood to equally apply to the monitoring device, to the monitoring system as well as to the method of monitoring operation. In particular, a mentioning of a component being configured or arranged to conduct a particular operation is to be understood to disclose a respective method step and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Arg-Leu-Phe-Ile-Phe-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a preferred embodiment of the invention will be described by making reference to the drawings, in which:

FIG. 2 is illustrative of a respective drug delivery device and further indicates positions of sensors and sound generating elements, FIG. 3 shows a diagram of a first, positive time delay, FIG. 4 shows a diagram of substantially zero time delay, FIG. 5 shows a diagram illustrating a negative time delay, FIG. 6 shows a diagram with a time delay indicating a dose dispensing operation and FIG. 7 shows a diagram representing irrelevant noise, FIG. 8 schematically shows relative position of sensors and sound generating elements in an initial configuration of the drug delivery device and FIG. 9 shows a comparative device after setting of a dose, FIG. 10 shows a schematic block diagram of the monitoring device to be acoustically and/or mechanically coupled with the drug delivery device.

DETAILED DESCRIPTION

Figure 1:
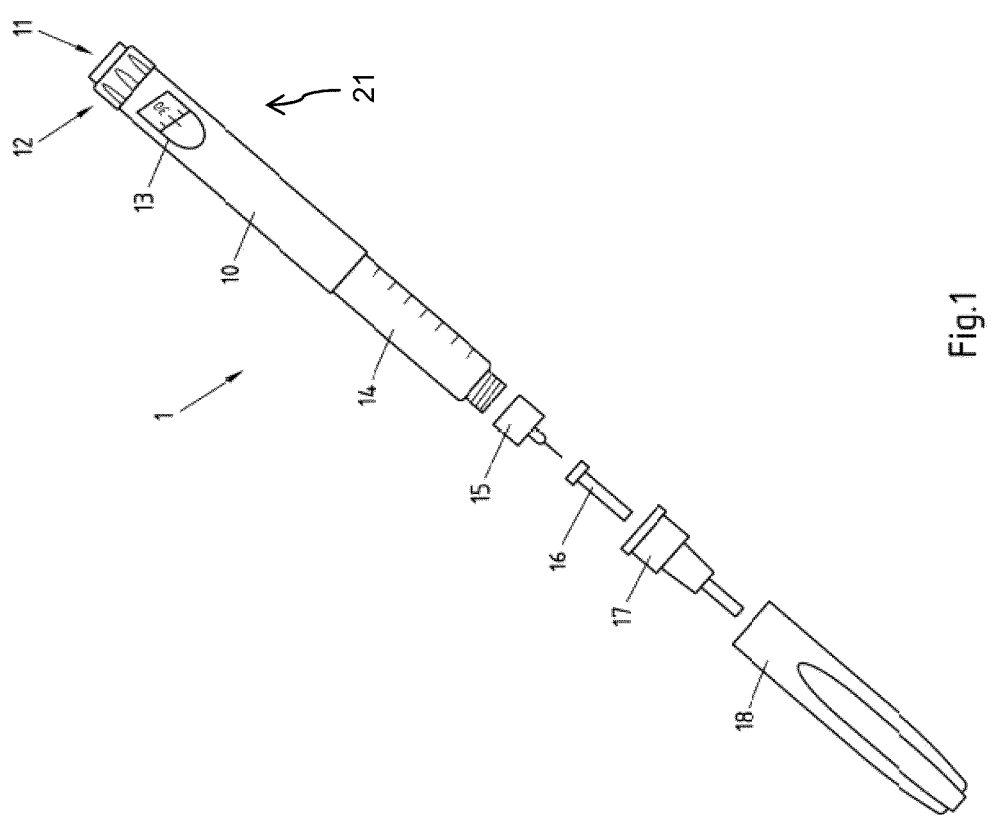
FIG. 1 shows a drug delivery device in form of a pen-type injector in a perspective exploded view.

FIG. 1 is illustrative of a drug delivery device 1 designed as a pen-type injector. The device comprises a proximal housing component 10 featuring a dosage window 13 through which the size of a set dose can be visually inspected. The housing 10 accommodates a drive mechanism 21 being not further illustrated here but which is to be operated by means of a dose dial 12 and by means of a injection button 11.

The housing 10 and its drive mechanism 21 is operably engaged with a cartridge 14 being filled with the medicament to be injected. Typically, the cartridge is disposed in a cartridge holder 19 as shown in FIG. 2 featuring at least one inspection window 20 allowing to visually inspect the filling level of the cartridge 14 disposed therein. The cartridge holder 19 or the cartridge 14 itself comprises a threaded socket portion at a distal outlet section in order to threadedly engage with a needle assembly 15 comprising a double-tipped injection needle. The replaceable and disposable injection needle 15 is provided with an inner needle cap 16 protecting the needle tip and further comprises an outer needle cap 17 that may serve as a package for the needle assembly 15.

The distal section of the drug delivery device 1 comprising the cartridge 14 and/or the cartridge holder 19 is further adapted to be protected and covered by a protective cap 18.

The present type of drug delivery device 1 may be implemented either as reusable device, wherein the cartridge 14 can be replaced when its content is used up. Alternatively, the drug delivery device can be designed as a disposable and all-mechanical device which is intended to be entirely discarded after consumption of the medicament provided in the cartridge 14. The drive mechanism 21 may resemble the one as disclosed for instance in EP 1 603 611 B1. Hence, for setting of a dose, the dose dial 12 may be turned in a screwed motion, thereby displacing the dose dial 12 and the injection button 11 in proximal direction 2, in which the dose dial 12 extends in longitudinal direction from the housing 10.

As further illustrated in FIG. 2, the drive mechanism 21 comprises two sound generating elements 22, 24 that generate a respective or characteristic click-sound either during dose setting or during dose dispensing. In the present embodiment, the distally located sound generating element 22 generates multiple or subsequent click-sounds during a dose setting operation. The proximally located sound generating element 24 is in turn adapted to generate at least one click-sound at the beginning, during or at the end of a dose dispensing operation, during which a user by exerting pressure in distal direction 3 returns the dose dial 12 back into its initial configuration as shown in FIGS. 2 and 8.

In FIG. 2, two sensors 23, 25 are illustrated that are adapted to detect audible signals generated by the two sound generating elements 22, 24 of the dose mechanism 21 of the drug delivery device 1. The two sensors 23, 25 belong to a monitoring device 40 as indicated in FIGS. 8 through 10, which is to be releasably coupled or connected to the housing 10 of the drug delivery device 1.

The drive mechanism 21, at least its dose dial sleeve 12 and the two sound generating elements 22, 24 are movably disposed relative to the housing 10 in longitudinal direction 2, 3. Hence, for dose setting, the drive mechanism 21 is displaced in proximal direction 2 and for dose dispensing, the drive mechanism 21 together with its sound generating elements 22, 24 returns to its initial configuration by a movement in distal direction 3.

As shown in FIGS. 2, 8 and 9, the first or distally located sound generating element 22 is located between the first and second sensors 23, 25. In the configuration according to FIGS. 2 and 8, longitudinal distance between sound generating element 22 and sensor 23 is smaller than the distance between element 22 and sensor 25. Therefore, with the beginning of a dose setting motion, the sensor 23 will receive the sound signal generated by the sound generating element 22 earlier than the second sensor 25.

Further and as indicated in FIGS. 8 and 9, the monitoring device 40 may comprise a third sensor 46, being e.g. implemented as optical sensor to visually detected a size of a set dosage. By way of the third sensor 46 additional information about the state of the drug delivery device 1 can be obtained that may be further used to process the signals obtained from the first and/or second sensors 23, 25. Moreover, by way if the third sensor 46, calibration of the monitoring device 40 can be provided in general.

The respective sensor signals are depicted in FIG. 3. The various sketches of FIGS. 3 to 7 show various diagrams 30, 32 of a electrical signals 31, 33 being generated by first and second sensors 23, 25, respectively. The situation as illustrated in FIG. 3 corresponds to the initial setting of FIG. 2. Hence, the signal 31 received and generated by sensor 23 advances the signal 33 generated by the proximally located sensor 25.

The time delay 36 between the two signals 31, 33 is indicative of the longitudinal position of sound generating element 22 relative to sensors 23, 25. The positive time delay 36 according to FIG. 3 is therefore indicative of a rather small dose size.

The diagrams 30, 32 of FIG. 4 relate to a configuration according to FIG. 9, wherein the sound generating element 22 is located almost in the middle between sensors 23, 25. Consequently, the two sensors 23, 25 receive the acoustical or vibrational signal almost at the same time. Consequently, the time delay 36 between signals 31' and 33' is almost zero and is therefore not further illustrated in FIG. 4.

The situation as illustrated in FIG. 5 corresponds to a rather large dose, wherein the dose dial and its dose sleeve 26 is displaced a maximum distance relative to the housing 10. Consequently, the sound generating element 22 is still located between sensors 23, 25 but is positioned much closer to sensor 25 than to sensor 23. Correspondingly, signal 33" of sensor 25 advances the signal 31" of sensor 23. A corresponding negative time delay 36' therefore arises being indicative of a rather large or maximum dose to be set by the present drive mechanism 21.

The proximally located sound generating element 24 is already located proximally from the distal sensor 25 in the initial configuration of the drive mechanism 21 as shown in FIGS. 2 and 8. It therefore lies outside the spatial region or outside the intermediate space formed by the two sensors 23 and 25. Even when the dose sleeve 26' is pulled out in distal direction 2 as shown in FIG. 9, the time delay 36" of a signal emanating from the sound generating element 24 substantially equals a pre-defined injection value (y), which is governed by the longitudinal distance between sensors 23, 25 and the velocity of sound propagation in the housing 10.

Typically, the pre-defined injection value (y) is larger than the maximum dosage value (x) that may originate from the distal sound generating element 22. This way, a dispensing operation accompanied by a click-sound originating from sound generating element 24 can be distinguished from dose setting operations accompanied by click-sounds originating from distal sound generating element 22 by a comparison of the time delay 36 with pre-defined dosage value x or pre-defined injection value y.

Apart from a time delay distinction it is also conceivable, that the click-sounds generated by the sound generating elements 22, 24 feature a different spectral range that can be accordingly detected by at least one of the sensors 23, 25.

FIG. 7 further shows a situation, wherein a time delay 36''' between signals 34 and 35 of sensors 23 and 25 exceeds the pre-defined dosage value x and/or the injection value y. Moreover, the delay 36''' is positive. Such a constellation neither matches with a dose setting operation nor with a dose dispensing operation and is therefore identified as irrelevant background noise. Since its origin must be located distally from the distal sensor 23 it may be generated in response of removal of any of the caps 16, 17, 18 of the drug delivery device 1. In particular when the detected and processed time delay exceeds a predefined value (y) or when signals derived from first and/or second sensors 23, 25 do not match with signals obtained e.g. from a third sensor 46, then the processing unit is adapted to classify the measured values as false and irrelevant.

As indicated in FIGS. 8, 9 and 10, the monitoring device 40 comprises a housing and is to be releasably connected with the housing 10 of the drug delivery device 1, e.g. by clips 28 or similar fastening members that provide sufficient sound transmission and sound propagation between the housings 10 and 40.

An example of the internal structure of the monitoring device 40 is further illustrated in FIG. 10. The two sensors 23, 25 are each coupled with a signal conditioning circuit 41, 42, for example a threshold circuit that may for instance comprise a Schmitt-trigger circuit. The output lines of the two signal conditioning circuits 41, 42 are coupled with a timer module 43 in such a way that any of the signals of sensors 23, 25 may start or stop the timer 43. If according to FIG. 3 signal 31 of sensor 23 starts the timer 43, the trailing signal 33 of sensor 25 subsequently stops the timer 43. Start and stop times are subtracted by the timer 43 to obtain a time delay 36 to be further processed by the processing unit 44. Event though the timer 43 and the processing unit 44 are illustrated separately in the present embodiment, those modules 43, 44 may also be integrated in a single processing unit, e.g. comprising a microcontroller.

The timer 43 and/or the processing unit 44 are adapted to detect and/or to distinguish temporal variations in the run-time of the signals 31, 33 in the range of nanoseconds.

The quality of the signal(s) obtained from the sensors 23, 25 depends on the kind of sensors used, the geometrical properties of involved parts like injection device, monitoring device or fastening element and also possible irrelevant noises. In order to prevent that the threshold circuit not reliably determines the acoustic signals, e.g. from sound generating elements, the monitoring device 40 may be equipped with analog signal conditioning means 41, 42 and digital signal processing means, located e.g. in the signal processing unit 44, for determination of the time delay. It if of further benefit when signals 31 and 33 are cross correlated prior and/or during signal processing to enable precise determination of run-time shifts or time delays.

The central processing unit 44 which may comprise a microcontroller or some other processing device may further be equipped with a storage module not further illustrated here for storing the time delay and/or a dose size related thereto. The processing unit 44 is further coupled with a user interface (UI) module 45. The UI module 45 may comprise one or more keys and a display, allowing to provide or to display information to the user, for example stored information or device related information, such as dose information, injection information and/or the like. For instance, the monitoring device 40 may indicate to the user, that the dose recently set should not be injected because it does not match with the prescription schedule. The user interface module 45 may therefore generate a respective alert, visually and/or audible.

Additionally, the processing unit 44 may distinguish between time delays 36, 36' being indicative of a dose size and such time delays 36" that correspond to an injection operation. Preferably, the processing unit 44 temporally stores those time delays 36, 36' that represent a dose size. Only in response to detection of an injection time-delay 36", the last dose size is transferred to the storage medium and stored therein. The storage medium is preferably of non-volatile type.

This way, even after setting of a dose, the set dosage may also be repeatedly amended. Hence, a constant or repeated but stepwise increase of the dose setting leads to a constant decrease of the time delay 36, 36'. Even in case a maximum dose has already been selected and set, corrections of the set dosage are always possible by turning the dose dial 12 in an opposite direction. Such counter-rotated movement in turn leads to a decrease of the time delay 36, 36'.

Additionally, the monitoring device 40 may be equipped with a sleeping functionality, wherein one of the sensors 23, 25 and/or an additional but not illustrated acceleration sensor can be used to observe the general handling of the drug delivery device. If the device is for instance gripped by a user, such activity can be detected by any of such sensor, thereby activating the monitoring device.

The invention claimed is:

1. A monitoring device for monitoring operation of a drug delivery device, wherein the drug delivery device comprises a drive mechanism operable to set and/or to dispense a dose of a medicament, wherein at least one of setting and dispensing of the dose is accompanied by a displacement or movement of a first signal generator of the drive mechanism along a first direction, wherein the first signal generator is configured to generate a first detectable signal when moving along the first direction, the monitoring device comprising:
  a first sensor configured to generate a first electrical signal in response to a detection of the first detectable signal emanating from the first signal generator when moving along the first direction;
  a second sensor arranged at a distance from the first sensor with regard to the first direction and being configured to generate a second electrical signal in response to a detection of the same first detectable signal emanating from the first signal generator; and
  a processing unit connected to the first sensor and to the second sensor, the processing unit being configured to receive the first electrical signal from the first sensor and the second electrical signal from the second sensor, the processing unit being configured to determine at least one of a dosing related parameter or a dispensing related status of the drug delivery device based on a time delay between receiving the first electrical signal and the second electrical signal.

2. The monitoring device according to claim 1, wherein at least one of the first sensor and the second sensor comprises at least one of an acoustic sensor, a vibration sensor, an acceleration sensor and a mechanical tension sensing element.

3. The monitoring device according to claim 1, wherein the processing unit is configured to determine a size of a dose set by the drug delivery device when the time delay is smaller than or equal to a predefined dosage value.

4. The monitoring device according to claim 1, wherein the processing unit is adapted to identify and/or to detect a dispensing operation of the drug delivery device when the time delay substantially equals a predefined injection value.

5. The monitoring device according to claim 1, wherein at least one of the first sensor, the second sensor and the processing unit is adapted to distinguish between the first detectable signal generated by the first signal generator and a second detectable signal generated by a second signal generator.

6. The monitoring device according to claim 1, wherein setting and/or dispensing of the dose is accompanied by the first detectable signal generated by the first signal generator when the first signal generator is subject to a displacement or movement along the first direction during setting of the dose and/or during dispensing of the dose.

7. The monitoring device according to claim 1, wherein the monitoring device is fastenable to a housing of the drug delivery device in a pre-defined position and/or pre-defined orientation, such that the first signal generator is movable along the first direction and is located between the first sensor and the second sensor with regard to the first direction.

8. The monitoring system according to claim 1, wherein the first signal generator is a click-sound generating component and the first detectable signal is a clicking sound.

9. The monitoring system according to claim 1, wherein the first detectable signal propagates from a housing of the drug delivery device to the monitoring device through a mechanical connection.

10. A monitoring system, comprising:
  a drug delivery device comprising a housing and a drive mechanism configured to interact with a cartridge containing a medicament to dispense, wherein the drive mechanism comprises a first signal generator movably disposed along a first direction relative to the housing during at least one of a dose setting operation and a dose dispensing operation, the first signal generator configured to generate a detectable signal when moving along the first direction; and
  a monitoring device, the monitoring device comprising:
    a first sensor configured to generate a first electrical signal in response to a detection of a detectable signal caused by a movement of the first signal generator relative to the housing during at least one of the dose setting operation and the dose dispensing operation,
    a second sensor arranged at a distance from the first sensor with regard to the first direction and configured to generate a second electrical signal in response to the detection of the same detectable signal caused by the movement of the first signal generator,
    wherein the first signal generator is operable to generate a detectable signal detectable by the first sensor and by the second sensor during at least one of the dose setting operation and the dose dispensing operation, and a processing unit connected to the first sensor and to the second sensor, the processing unit being configured to receive the first electrical signal from the first sensor and the second electrical signal from the second sensor and determine at least one of a dosing related parameter or dispensing related status of the drug delivery device based on a time delay between receiving the first electrical signal and the second electrical signal.

11. The monitoring system according to claim 10, wherein the first signal generator is adapted to generate a first audible or acoustic signal during the dose setting operation of the drive mechanism.

12. The monitoring system according to claim 10, wherein the drive mechanism comprises at least a second signal generator adapted to generate a second audible or acoustic signal during the dose dispensing operation of the drive mechanism.

13. The monitoring system according to claim 10, wherein the monitoring device is fastenable to the housing of the drug delivery device in a predefined position such that the first signal generator of the drive mechanism is located between the first sensor and the second sensor with regard to the first direction.

14. The monitoring system according to claim 10, wherein the monitoring device is fastenable to the housing of the drug delivery device in a predefined position such that the first signal generator of the drive mechanism is located outside an intermediate space between the first sensor and the second sensor of the monitoring device with regard to the first direction.

15. The monitoring system according to claim 10, wherein the first signal generator is a click-sound generating component and the detectable signal is a clicking sound.

16. The monitoring system according to claim 10, wherein the first detectable signal propagates from the housing of the drug delivery device to the monitoring device through a mechanical connection.

17. A method of monitoring operation of a drug delivery device, the drug delivery device comprising a housing and a drive mechanism, the drive mechanism comprising at least a first signal generator movably disposed along a first direction relative to the housing, the method comprising:

generating an audible or acoustic signal by the first signal generator when the first signal generator moves along the first direction during at least one of setting and dispensing of a dose;

detecting the same audible or acoustic signal by both a first sensor and by a second sensor of a monitoring device, wherein the first sensor and the second sensor are arranged at a distance from each other with regard to the first direction;

generating a first electrical signal by the first sensor and generating a second electric signal by the second sensor;

receiving the first electrical signal and the second electrical signal by a processing unit;

determining a time delay between the first electrical signal and the second electrical signal by the processing unit; and determining at least one dosing related parameter or dispensing related status of the drug delivery device based on the time delay.

18. The method according to claim 17, further comprising:

comparing a magnitude of the time delay with at least one of a predefined dosage value and/or injection value; and determining a size of a set dose and/or identifying and/or detecting a dispensing operation of the drug delivery device based on the comparison.

19. A monitoring system, comprising:

a drug delivery device comprising a housing and a drive mechanism configured to interact with a cartridge containing a medicament to dispense, wherein the drive mechanism comprises a first signal generator movably disposed along a first direction relative to the housing during operation of the drug delivery device; and a monitoring device, the monitoring device comprising:

a first sensor configured to generate a first electrical signal in response to a movement of the first signal generator relative to the housing during operation of the drug delivery device, a second sensor arranged at a distance from the first sensor and configured to generate a second electrical signal in response to the movement of the first signal generator, wherein the first signal generator is operable to generate a detectable signal detectable by the first sensor and by the second sensor during operation of the drug delivery device, wherein the first signal generator is adapted to generate a first audible or acoustic signal during a dose setting operation of the drive mechanism, and a processing unit connected to the first sensor and to the second sensor, the processing unit being configured to receive the first electrical signal from the first sensor and the second electrical signal from the second sensor and determine at least one of a dosing related parameter or dispensing related status of the drug delivery device based on a time delay between receiving the first electrical signal and the second electrical signal.

\* \* \* \* \*

UNITED STATES PATENT AND TRADEMARK OFFICE
CERTIFICATE OF CORRECTION

PATENT NO. : 11,315,670 B2
APPLICATION NO. : 16/520732
DATED : April 26, 2022
INVENTOR(S) : Alexander Allerdings Page 1 of 1

It is certified that error appears in the above-identified patent and that said Letters Patent is hereby corrected as shown below:

On the Title Page

Column 1, (30), under Foreign Application Priority Data, delete "1180590" and insert -- 11180590.9 --

In the Claims

Column 16, Line 36, Claim 8, delete "system" and insert -- device --

Column 16, Line 39, Claim 9, delete "system" and insert -- device --

Signed and Sealed this
Twenty-first Day of June, 2022

Katherine Kelly Vidal
*Director of the United States Patent and Trademark Office*